US012127858B2

(12) United States Patent
Park et al.

(10) Patent No.: US 12,127,858 B2
(45) Date of Patent: *Oct. 29, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 78 days.

This patent is subject to a terminal disclaimer.

(21) Appl. No.: 17/828,786

(22) Filed: May 31, 2022

(65) Prior Publication Data
US 2022/0287655 A1 Sep. 15, 2022

Related U.S. Application Data

(62) Division of application No. 16/128,060, filed on Sep. 11, 2018, now Pat. No. 11,382,572.

(30) Foreign Application Priority Data
Sep. 13, 2017 (KR) .................. 10-2017-0116935

(51) Int. Cl.
A61B 5/00 (2006.01)
A61B 5/02 (2006.01)
(Continued)

(52) U.S. Cl.
CPC ........ A61B 5/7278 (2013.01); A61B 5/02007 (2013.01); A61B 5/02116 (2013.01);
(Continued)

(58) Field of Classification Search
None
See application file for complete search history.

(56) References Cited

U.S. PATENT DOCUMENTS 6,694,265 B2 2/2004 Gorenstein
7,544,168 B2 * 6/2009 Nitzan ................... A61B 5/021
600/490
(Continued)

FOREIGN PATENT DOCUMENTS

CA 2 994 341 A1 12/2016
JP 2008-289632 A 12/2008
(Continued)

OTHER PUBLICATIONS

"Seamless Healthcare Monitoring, Advancement in wearable, attachable, and invisible devices". Tamura et al., Ed. Springer 2018. Part III, Chapter 6 (Year: 2018).*
(Continued)

Primary Examiner — Yi-Shan Yang
(74) Attorney, Agent, or Firm — Sughrue Mion, PLLC

(57) ABSTRACT

An apparatus for non-invasively estimating bio-information may include a bio-signal acquirer configured to acquire a bio-signal; and a processor configured to extract a plurality of characteristic points from the bio-signal, determine internally dividing points of the plurality of characteristic points, and extract feature values from the bio-signal based on the internally dividing points to perform bio-information estimation. The plurality of characteristic points may include a first time point and a second time point when the pulse wave signal includes a first component pulse wave that has a maximum amplitude at the first time point, and a second component pulse wave that has a maximum amplitude at the second time point.

6 Claims, 18 Drawing Sheets

(51) Int. Cl.
  *A61B 5/021* (2006.01)
  *A61B 5/024* (2006.01)
  *A61B 5/16* (2006.01)
  *G16H 50/20* (2018.01)

(52) U.S. Cl.
  CPC ...... *A61B 5/02125* (2013.01); *A61B 5/02416* (2013.01); *A61B 5/165* (2013.01); *G16H 50/20* (2018.01)

(56) References Cited

U.S. PATENT DOCUMENTS

| | | | |
|---|---|---|---|
| 7,566,307 | B2 | 7/2009 | Inukai et al. |
| 8,285,369 | B2 | 10/2012 | Kuo et al. |
| 8,478,389 | B1 | 7/2013 | Brockway et al. |
| 8,758,259 | B2 | 6/2014 | Suzuki |
| 10,111,596 | B2 | 10/2018 | Kang et al. |
| 2010/0081947 | A1 | 4/2010 | Suzuki |
| 2012/0143012 | A1* | 6/2012 | Watson .................. G16H 50/20 600/300 |
| 2013/0116580 | A1 | 5/2013 | Liu et al. |
| 2015/0257653 | A1 | 9/2015 | Hyde et al. |
| 2016/0063233 | A1 | 3/2016 | Bae et al. |
| 2017/0132384 | A1 | 5/2017 | Park et al. |
| 2018/0146865 | A1 | 5/2018 | Ortlepp |
| 2020/0037902 | A1 | 9/2020 | De Haan |

FOREIGN PATENT DOCUMENTS

| | | |
|---|---|---|
| JP | 2010-213809 A | 9/2010 |
| KR | 10-2006-0119472 A | 11/2006 |
| KR | 10-2008-0044224 A | 6/2008 |
| KR | 10-2011-0032107 A | 3/2011 |
| KR | 10-1503604 B1 | 3/2015 |
| KR | 10-2016-0146394 A | 12/2016 |
| KR | 10-1724282 B1 | 4/2017 |
| WO | 2011/150585 A1 | 12/2011 |

OTHER PUBLICATIONS

Communication issued Mar. 29, 2022 by the Korean Intellectual Property Office in counterpart Korean Patent Application No. 10-2017-0116935.

Communication dated Jan. 23, 2019, issued by the European Patent Office in counterpart European Application No. 18191397.1.

* cited by examiner

APPARATUS AND METHOD FOR ESTIMATING BIO-INFORMATION

CROSS-REFERENCE TO RELATED APPLICATION(S)

This application is a divisional application of U.S. application Ser. No. 16/128,060, filed Sep. 11, 2018, which claims priority from Korean Patent Application No. 10-2017-0116935, filed on Sep. 13, 2017 in the Korean Intellectual Property Office, the disclosures of which are incorporated herein by reference in their entireties.

BACKGROUND

1. Field

Apparatuses and methods consistent with exemplary embodiments relate to non-invasively estimating bio-information.

2. Description of Related Art

Research on information technology (IT)-medical convergence technology, in which IT and medical technology are combined, is being recently carried out to address the aging population structure, rapid increase in medical expenses, and shortage of specialized medical service personnel. In particular, monitoring of a health status of a human body is not limited to being performed only at a fixed place, such as a hospital, but is expanded to a mobile healthcare sector for monitoring a user's health status at any time and any place in daily life at home and office. Electrocardiography (ECG), photoplethysmogram (PPG), and electromyography (EMG) signals are examples of bio-signals that indicate the individual's health condition. A variety of signal sensors are being developed to measure such signals in daily life. Especially, in the case of a PPG sensor, it is possible to estimate blood pressure of a human body by analyzing a form of pulse wave that reflects a cardiovascular state.

According to a PPG bio-signal related research, the whole PPG signal is a summation of a propagation wave propagating from the heart to peripheral parts of a body and reflection waves returning from the peripheral parts of the body. It is known that information to be used to estimate blood pressure can be acquired by extracting various features related to propagation waves or reflection waves.

SUMMARY

According to an aspect of an exemplary embodiment, there is provided an apparatus for estimating bio-information, including: a bio-signal acquirer configured to acquire a bio-signal; and a processor configured to extract a plurality of characteristic points from the bio-signal, determine internally dividing points of the plurality of characteristic points, and extract feature values from the bio-signal based on the internally dividing points to perform bio-information estimation.

The processor may include an internally dividing point calculator configured to apply weights respectively to time values of the plurality of characteristic points and calculate the internally dividing points of the plurality of characteristic points based on the time values to which the weights are applied.

The internally dividing point calculator may be further configured to calculate the internally dividing points of the plurality of characteristic points based on a sum of the weights.

The internally dividing point calculator may be further configured to apply the weights respectively to the time values based on amplitude values of the plurality of characteristic points.

The internally dividing point calculator may be further configured to calculate the weights based on differences between first amplitudes at a plurality of points in a derivative signal of the bio-signal and a second amplitude at a predetermined point in the derivative signal, and wherein the plurality of points in the derivative signal may correspond to the plurality of characteristic points extracted from the bio-signal.

The processor may include a bio-information estimator configured to estimate bio-information comprising at least one of blood pressure, vascular age, arterial stiffness, aortic pressure waveform, stress index, and fatigue based on the extracted feature values.

The processor may include a characteristic point extractor configured to extract, as the plurality of characteristic points, at least one of points associated with component pulses constituting the bio-signal, a point at which an amplitude has a maximum value in a systolic region of the bio-signal, and an area of the bio-signal.

The characteristic point extractor may be further configured to determine local minimum points in a second derivative signal of the bio-signal as the points associated with the component pulses.

The processor may further include a feature extractor configured to extract the feature values based on at least one of a ratio of the area of the bio-signal to an amplitude value at the point at which an amplitude has the maximum value in the systolic region of the bio-signal and a difference in time value between the internally dividing points acquired from each of the systolic region and a diastolic region of the bio-signal.

The bio-signal acquirer may include a photoplethysmogram (PPG) sensor configured to emit a light to an object and acquire a PPG signal by detecting the light reflected or scattered from the object.

The apparatus may further include a communication interface configured to receive a PPG signal from an external device and transmit the PPG signal to the bio-signal acquirer.

The bio-signal acquirer may include a light source configured to emit a light to an object and a detector configured to detect the light scattered or reflected from the object, and wherein the bio-signal acquirer may acquire the bio-signal from the light detected by the detector.

According to an aspect of another exemplary embodiment, there is provided a method of estimating bio-information, including: acquiring a bio-signal; extract a plurality of characteristic points from the bio-signal; determining internally dividing points of the plurality of characteristic points; and extracting feature values from the bio-signal based on the internally dividing points to perform bio-information estimation.

The determining the internally dividing points may include applying weights respectively to time values of the plurality of characteristic points and calculating the internally dividing points of the plurality of characteristic points based on the time values to which the weights are applied.

The determining the internally dividing points may include calculating the internally dividing points of the plurality of characteristic points based on a sum of the weights.

The determining the internally dividing points may include applying the weights respectively to the time values based on amplitude values of the plurality of characteristic points.

The determining the internally dividing points may include applying the weights respectively to the time values based on differences between first amplitudes at a plurality of points in a derivative signal of the bio-signal and a second amplitude at a predetermined point in the derivative signal, and wherein the plurality of points in the derivative signal may correspond to the plurality of characteristic points extracted from the bio-signal.

The method may further include estimating the bio-information, which includes at least one of blood pressure, vascular age, arterial stiffness, aortic pressure waveform, stress index, and fatigue, based on the extracted feature values.

The method may further include extracting, as the plurality of characteristic points, at least one of points associated with component pulses constituting the bio-signal, a point at which an amplitude has a maximum value in a systolic region of the bio-signal, and an area of the bio-signal.

The extracting of the characteristic points may include determining local minimum points in a second derivative signal of the bio-signal as the points associated with the component pulses.

The extracting the feature values may include extracting the feature values based on at least one of a ratio of the area of the bio-signal to an amplitude value at the point at which an amplitude has the maximum value in the systolic region of the bio-signal and a difference in time value between the internally dividing points acquired from each of the systolic region and a diastolic region of the bio-signal.

According to an aspect of another exemplary embodiment, there is provided a blood pressure monitoring device, including: a light emitter configured to emit a light to a subject; a light detector configured to detect the light that is scattered, deflected, or reflected from the subject to obtain a pulse wave signal from the detected light; a processor configured to extract a plurality of characteristic points from the pulse wave signal, determine amplitude values corresponding to the plurality of characteristic points from the pulse wave signal, determine an internally dividing point of the plurality of characteristic points based on the amplitude values and the plurality of characteristic points, and determine a blood pressure of the subject based on the internally dividing point of the pulse wave signal.

The processor may be further configured to: extract a first time point $T_1$ and a second time point $T_2$ from the pulse wave signal, as the plurality of characteristic points, when the pulse wave signal comprises a first component pulse wave that has a maximum amplitude at the first time point $T_1$, and a second component pulse wave that has a maximum amplitude at the second time point $T_2$; determine a first amplitude $P_1$ and a second amplitude $P_2$ of the pulse wave signal corresponding to the first time point $T_1$ and the second time point $T_2$, respectively; and determine the internally dividing point based on the first time point $T_1$, the second time point $T_2$, the first amplitude $P_1$, and the second amplitude $P_2$.

The processor may be further configured to: extract a first time point $T_1$ and a maximum time point $T_{max}$ from the pulse wave signal, as the plurality of characteristic points, when the pulse wave signal comprises a first component pulse wave that has a maximum amplitude at the first time point $T_1$, and the pulse wave signal has a maximum amplitude $P_{max}$ at the maximum time point $T_{max}$; determine a first amplitude $P_1$ of the pulse wave signal corresponding to the first time point $T_1$; and determine the internally dividing point based on the first time point $T_1$, the maximum time point $T_{max}$, the first amplitude $P_1$ and the maximum amplitude $P_{max}$.

The processor may be further configured to: extract a third time point $T_3$ and a fourth time point $T_4$ from the pulse wave signal, as the plurality of characteristic points, when the pulse wave signal comprises a third component pulse wave that has a maximum amplitude at the third time point $T_3$, and a fourth component pulse wave that has a maximum amplitude at the fourth time point $T_4$; determine a third amplitude $P_3$ and a fourth amplitude $P_4$ of the pulse wave signal corresponding to $T_3$ and $T_4$, respectively; and determine the internally dividing point based on the third time point $T_3$, the fourth time point $T_4$, the third amplitude $P_3$, and the fourth amplitude $P_4$, in response to the fourth amplitude $P_4$ being greater than the third amplitude $P_3$.

The processor may be further configured to: extract a third local minimum point $T_{local3}$ and a fourth local minimum point $T_{local4}$ from a second derivative signal of the pulse wave signal; extract, from the second derivative signal, a third local maximum point $L_3$ that appears prior to the third local minimum point $T_{local3}$, and a fourth local maximum point $L_4$ that appears between the third local minimum point $T_{local3}$ and the fourth local minimum point $T_{local4}$; determine a first difference $W_1$ between an amplitude at the third local minimum point $T_{local3}$ and an amplitude at the fourth local maximum point $L_4$; determine a second difference $W_2$ between the amplitude at the fourth local maximum point $L_4$ and an amplitude at the fourth local minimum point $T_{local4}$; and determine the internally dividing point based on the third local minimum point $T_{local3}$, the fourth local minimum point $T_{local4}$, the first difference $W_1$, and the second difference $W_2$.

The processor may be further configured to: extract a third local minimum point $T_{local3}$ and a fourth local minimum point $T_{local4}$ from a second derivative signal of the pulse wave signal; extract, from the second derivative signal, a third local maximum point $L_3$ that appears prior to the third local minimum point $T_{local3}$, and a fourth local maximum point $L_4$ that appears between the third local minimum point $T_{local3}$ and the fourth local minimum point $T_{local4}$; determine a first difference $W_1$ between an amplitude at the third local maximum point $L_3$ and an amplitude at the third local minimum point $T_{local3}$; determine a second difference $W_2$ between the amplitude at the third local maximum point $L_3$ and the amplitude at the fourth local minimum point $T_{local4}$; and in response to the first difference $W_1$ being less than a predetermined threshold value, determine the internally dividing point based on the third local minimum point $T_{local3}$, the fourth local minimum point $T_{local4}$, the first difference $W_1$, and the second difference $W_2$.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
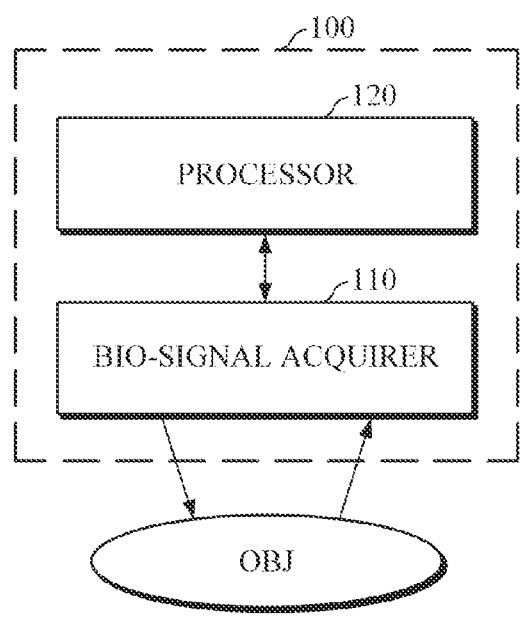
FIG. 1 is a block diagram illustrating an apparatus for estimating bio-information according to one exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as " . . . unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list.

FIG. 1 is a block diagram illustrating an apparatus for estimating bio-information according to one exemplary embodiment. The apparatus 100 for estimating bio-information of the present exemplary embodiment may be implemented as a hardware device to be mounted in a terminal, such as a smartphone, a tablet personal computer (PC), a desktop PC, a notebook PC, or the like, or an independent hardware device. When the apparatus 100 is implemented as an independent hardware device, the apparatus 100 may have the form of a wearable device that a user (e.g., an object OBJ) can easily measure bio-information while carrying the device. For example, the hardware device may be implemented as a wearable device of a wristwatch type, a bracelet type, a wristband type, a ring type, a glass type, or a hairband type. However, the type of wearable device is not limited to the above examples, and the wearable device may be modified according to various purposes, for example, it may be manufactured as a fixed type for utilizing bio-information in a medical institution for measurement and analysis.

Referring to FIG. 1, the apparatus 100 for estimating bio-information includes a bio-signal acquirer 110 and a processor 120.

The bio-signal acquirer 110 may acquire a bio-signal from an object OBJ as shown in FIG. 1 and transmit the acquired bio-signal to the processor 120. In this case, the bio-signal may be a photoplethysmogram (PPG) signal (hereafter referred to as a "pulse wave signal"). However, the bio-signal is not limited thereto and may include various bio-signals, such as an electrocardiography (ECG) signal, a PPG signal, an electromyography (EMG) signal, and the like, which can be modeled by a plurality of waveform components.

For example, the bio-signal acquirer 110 may include a spectrometer or a PPG sensor configured to measure a PPG signal. The PPG sensor may include a light source configured to emit light to the object OBJ and a detector configured to measure a PPG signal by detecting light scattered or reflected from tissues of the irradiated object OBJ. In this case, the light source may include at least one of a light emitting diode, a laser diode, and a phosphor, but is not limited thereto. The detector may include a photodiode.

The processor 120 may generate a control signal to drive the bio-signal acquirer 110. Upon receiving the control signal from the processor 120, the bio-signal acquirer 110 may emit a light to the object OBJ and receive the light that is reflected from the OBJ. The bio-signal acquire 110 may acquire a pulse wave signal (i.e., a PPG signal) from the received light. The object is a living body which can be in touch with or adjacent to the PPG sensor and may be a part of a human body which is easy to measure a PPG signal. For example, the object OBJ may be an area of a wrist surface adjacent to a radial artery and may include an upper part of a wrist where venous blood or capillary blood passes. When a pulse wave is measured at a skin surface of the wrist under which the radial artery passes, the influence of external factors, such as the thickness of the skin tissue inside the wrist, which cause a measurement error can be relatively small. However, the object OBJ is not limited to the above examples, and may be a peripheral region of a human body, such as a finger, a toe, or the like, which is a region having a high blood vessel density in the human body.

When acquiring the bio-signal, the bio-signal acquirer 110 may perform preprocessing on the bio-signal, such as filtering for removing noise from the acquired bio-signal, amplification of the bio-signal, or converting the bio-signal into a digital signal.

When the processor 120 receives a request for bio-signal estimation from the user, the processor 120 may generate a control signal to control the bio-signal acquirer 110, and transmit the control signal to the bio-signal acquirer 110. In addition, the processor 120 may receive the bio-signal from the bio-signal acquirer 110 and acquire bio-information by analyzing the received bio-signal. In this case, the bio-information may include a blood pressure, vascular age, arterial stiffness, aortic pressure waveform, stress index and fatigue, but is not limited thereto.

When the processor 120 receives the bio-signal from the bio-signal acquirer 110, the processor 120 may extract features necessary for bio-information estimation by analyzing a waveform of the received bio-signal. To this end, the processor 120 may extract a plurality of characteristic points from the received bio-signal and extract the features using the extracted characteristic points.

For example, the processor 120 may extract points associated with a plurality of component pulses constituting the waveform of the entire bio-signal as the characteristic points. In addition, the processor 120 may calculate internally dividing points of characteristic points. The processor 120 may use any one or any combination of the characteristic points and the internally dividing points to extract features for bio-information estimation. As such, the internally dividing point is calculated from the characteristic points initially extracted from the bio-signal and is used along with the characteristic points to extract additional features that may be used to perform bio-information estimation. Accordingly, it may be possible to obtain a more accurate feature even when the initially extracted characteristic points are extracted from an instable waveform under a non-ideal environment, such as motion noise or sleep.

Figure 2:
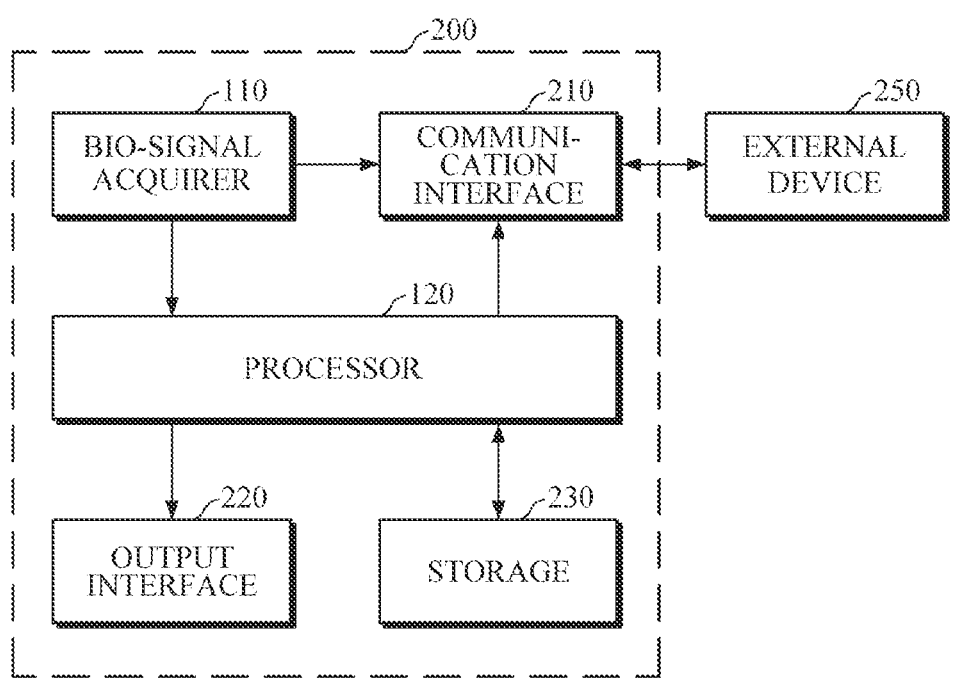
FIG. 2 is a block diagram illustrating an apparatus for estimating bio-information according to another exemplary embodiment.

FIG. 2 is a block diagram illustrating an apparatus for estimating bio-information according to another exemplary embodiment.

Referring to FIG. 2, an apparatus 200 for estimating bio-information includes a bio-signal acquirer 110, a processor 120, a communication interface 210, an output interface 220, and a storage 230.

The bio-signal acquirer 110 may acquire a bio-signal of an object from an external device 250. For example, the bio-signal acquirer 110 may acquire a bio-signal from the external device 250 through the communication interface 210 without being equipped with a bio-signal measurement sensor, such as a PPG sensor. Alternatively, when the bio-signal acquirer 110 is equipped with the bio-signal measurement sensor, such as a PPG sensor, the bio-signal acquirer 110 may selectively use a method of acquiring a bio-signal from the external device 250 under the control of the processor 120 or acquiring a bio-signal by directly driving the bio-signal measurement sensor.

The bio-signal acquirer 110 may perform a preprocessing operation to remove noise from the bio-signal received from the external device 250 and convert the bio-signal into a digital signal, and then may transmit the processed bio-signal to the processor 120.

The processor 120 may generate a control signal to control the bio-signal acquirer 110 in order to acquire the bio-signal. In addition, when the bio-signal is to be acquired from the external device 250, the processor 120 may control the communication interface 210 to be connected to the external device 250.

The apparatus 200 may be connected to the external device 250 through the communication interface 213, using access information of the external device 250 that is included in the control signal. Once the apparatus 200 is connected to the external device 250, the apparatus 200 210 may receive the bio-signal from the external device 250 and then transmit the bio-signal to the bio-signal acquirer 110, through the communication interface 210. In this case, the external device 250 may include a bio-signal measurement sensor to directly measure a bio-signal from the object, or may be a device that receives a bio-signal from a bio-signal measurement device and stores the received bio-signal.

In particular, the communication technology may include a Bluetooth communication, a Bluetooth low energy communication, a near field communication (NFC), a wireless local area network (WLAN) communication, a ZigBee communication, an infrared data association (IrDA) communication, a Wi-Fi direction communication, an ultra-wideband (UWB) communication, Ant+ communication, a Wi-Fi communication, and a mobile communication technology, but is not limited thereto.

When receiving the bio-signal from the bio-signal acquirer 110, the processor 120 may analyze the bio-signal to extract characteristic points and extract features that may be necessary for bio-signal estimation using the extracted characteristic points. In this case, when a waveform of the bio-signal exhibits a non-ideal and unstable form, the processor 120 may calculate internally dividing points using the extracted characteristic points and use the calculated internally dividing points along with the characteristic points to extract features.

When the features are extracted, the processor 120 may estimate bio-information using the extracted feature. In this case, the bio-information may be estimated using a previously constructed bio-information estimation model.

The output interface 220 may output and provide the acquired bio-signal information and various processing results of the processor 120. The output interface 220 may provide the information to the user through various visual/non-visual methods using a display module, a speaker, and a haptic device mounted in the device.

For example, when a blood pressure of the user is estimated, the output interface 220 may output the estimated blood pressure to the user using various visual methods, such as a color, a thickness of a line, a font, and the like, based on whether the estimated blood pressure is within or out of a normal range. Alternatively, the estimated blood pressure may be output by voice or through a non-visual method in which vibration or tactile sensation is changed according to the abnormality of the blood pressure. Alternatively, when it is determined that the estimated blood pressure is abnormal when compared with the recent history of measurement, the user may be warned or advised about actions to be taken by providing, for example, cautionary food information or information about a hospital to be reserved.

The storage 230 may store various pieces of reference information required for bio-information estimation, the obtained bio-signal, the extracted characteristic points and internally dividing points, the extracted features, bio-information estimation results, and the like. In this case, the various pieces of reference information required for bio-information estimation may include user information, such as an age, sex, occupation, current health status, and the like, and the bio-information estimation model information, but is not limited thereto. The storage 230 may include a storage medium of at least one type of a flash memory type, a hard disk type, a multimedia card micro type, a card-type memory (e.g., Secure Digital or eXtreme Digital memory, etc.) a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk.

Meanwhile, when there is a request from the external device 250 through the communication interface 210, the processor 120 may request the external device 250 to estimate bio-information by transmitting information about at least one of the extracted characteristic points, the internally dividing points, and the extracted feature to the external device 250. However, aspects of the present disclosure are not limited thereto, and when the external device 250 is a device having a relatively better computing performance and equipped with a bio-information estimation function, the external device 250 may request the bio-information estimation by transmitting the characteristic points, internally dividing points, or feature information.

Figure 3:
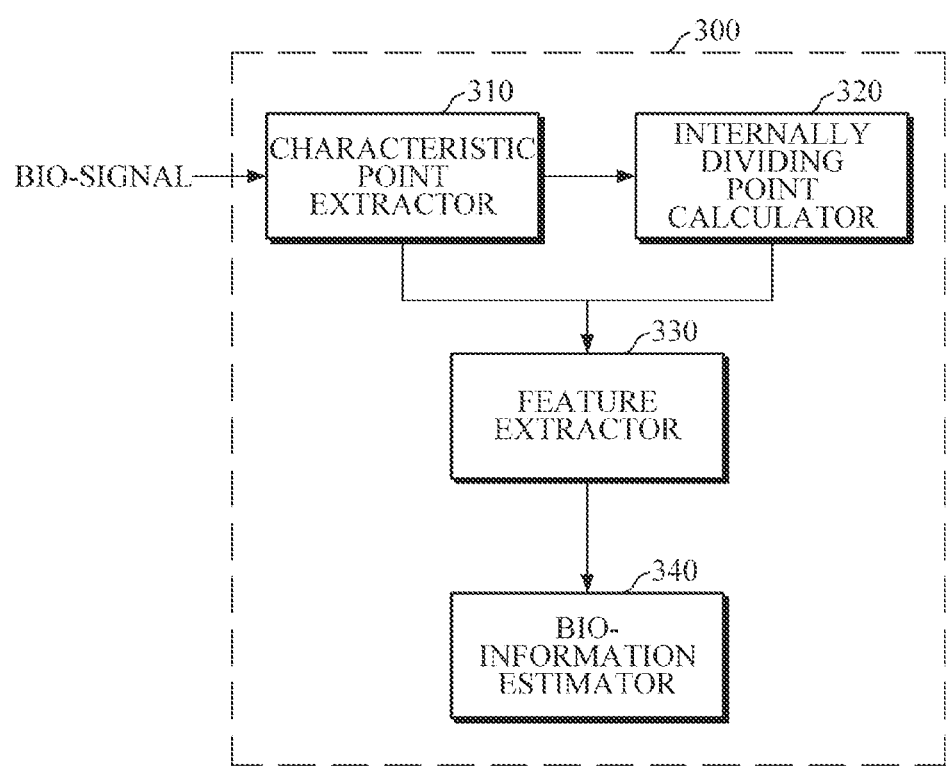
FIG. 3 is a block diagram illustrating a processor according to the exemplary embodiments of FIGS. 1 and 2.
Figure 4A:
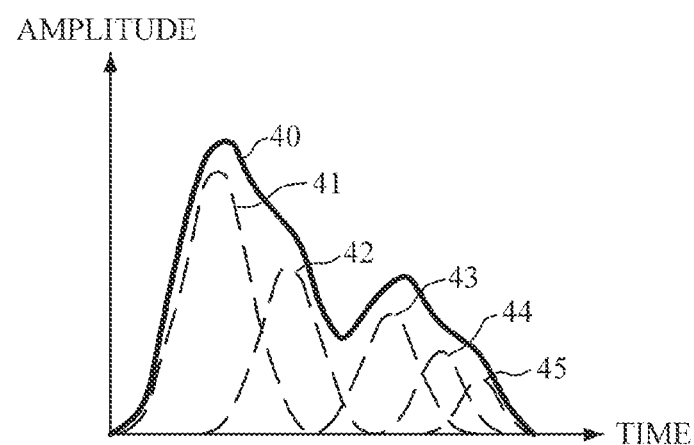
FIGS. 4A, 4B, and 4C are diagrams for describing an exemplary embodiment in which characteristic points are extracted from a bio-signal.
Figure 4B:
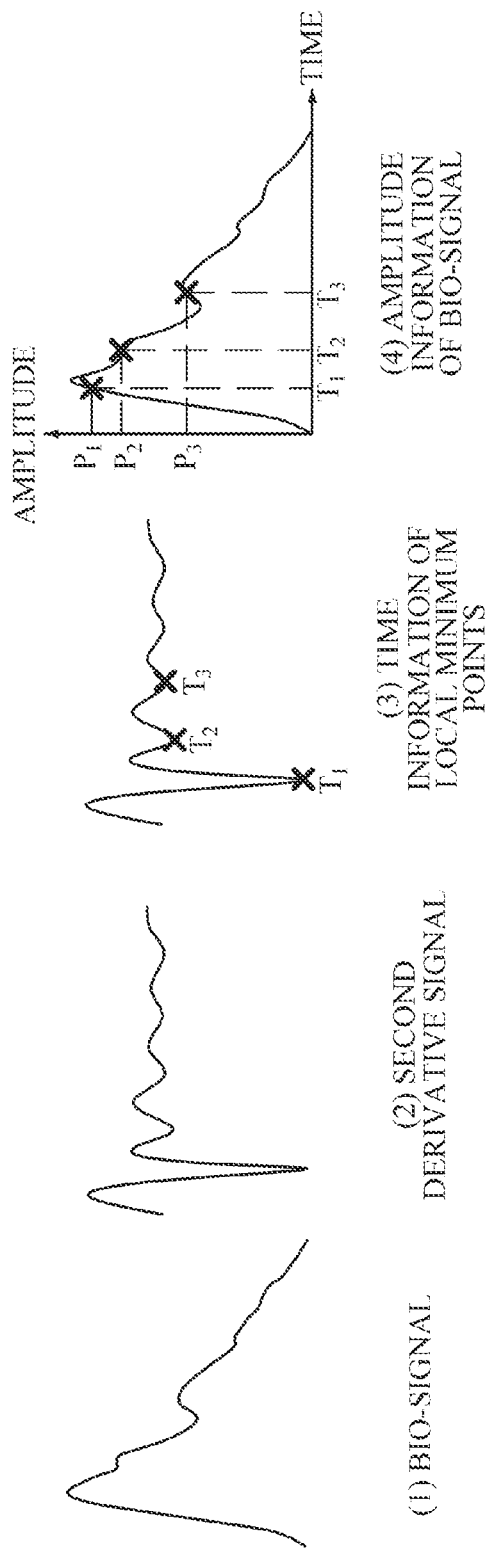
Figure 4C:
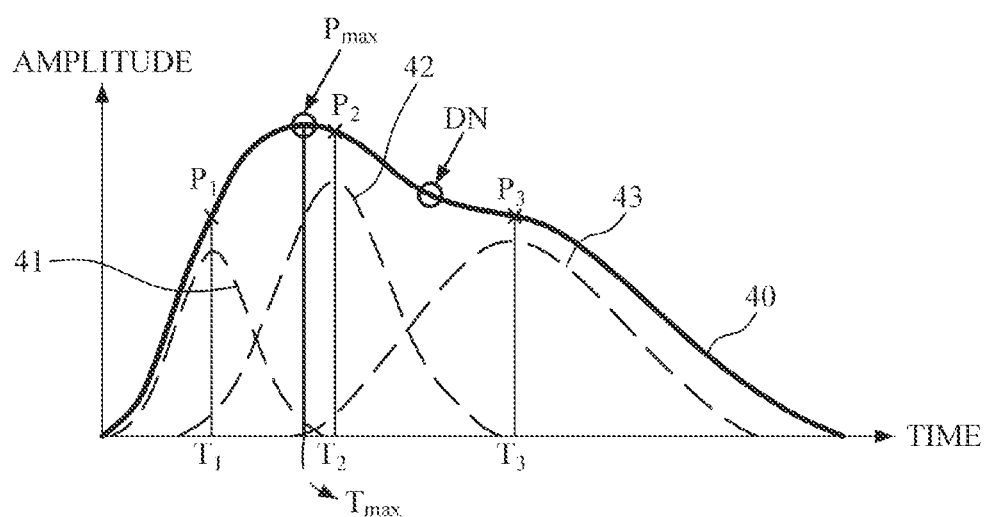

FIG. 3 is a block diagram illustrating the processor according to the exemplary embodiments of FIGS. 1 and 2. FIGS. 4A to 4C are diagrams for describing an exemplary embodiment in which characteristic points are extracted from a bio-signal. FIGS. 5A to 5E are diagrams for describing an exemplary embodiment in which internal dividing points are calculated using the characteristic points of the bio-signal.

An exemplary embodiment in which features necessary for bio-information estimation are extracted through characteristic point extraction, internally dividing point calculation, and the calculated internally dividing points will be described with reference to FIGS. 3 to 5E. Hereinafter, for convenience of description, it will be assumed that an acquired bio-signal is a pulse wave signal and the bio-information to be estimated is blood pressure.

As shown in FIG. 3, a processor 300 includes a characteristic point extractor 310, an internally dividing point calculator 320, a feature extractor 330, and a bio-information estimator 340.

The characteristic point extractor 310 may extract characteristic points using the bio-signal acquired from an object. For example, the characteristic point extractor 310 may extract points associated with component pulses constituting the bio-signal as characteristic points.

Generally, the pulse wave signal acquired from the object may be a summation of a propagation wave propagating from the heart to peripheral parts of a body and reflection waves returning from the peripheral parts of the body. FIG. 4A illustrates a pulse wave signal 40 which is a summation of five component pulses 41, 42, 43, 44, and 45. When information about points associated with each of the component pulses 41, 42, 43, 44, and 45, for example, time and amplitude information may be extracted as characteristic points and the extracted characteristic points are appropriately combined, a feature with high correlation with blood pressure may be extracted. Generally, up to third component pulses are mainly used to estimate blood pressure. Subsequent pulses may not be observed because it may be difficult to detect the subsequent pulses due to noise. Also, the subsequent pulses may have low correlation with blood pressure estimation.

FIG. 4B illustrates an example of extracting points associated with component pulses as characteristic points from a pulse wave signal using a second derivative signal of a bio-signal. Referring to FIG. 4B, when a bio-signal is acquired as shown in (1) BIO-SIGNAL, the characteristic point extractor 310 may derive a second derivative signal by differentiating the bio-signal as shown in (2) SECOND DERIVATIVE SIGNAL, search for local minimum points from the derived second derivate signal as shown in (3) TIME INFORMATION OF LOCAL MINIMUM POINTS, and extract time points $T_1$, $T_2$, and $T_3$ corresponding to the local minimum points as the characteristic points, as shown in (4) AMPLITUDE INFORMATION OF BIO-SIGNAL. In addition, the characteristic point extractor 310 may extract, from the entire bio-signal, amplitudes $P_1$, $P_2$, and $P_3$ corresponding to the time points $T_1$, $T_2$, and $T_3$ extracted from the derivative signal as characteristic points. The local minimum point may refer to a specific point of a part of the second derivative signal where the signal decreases and increases again, that is, a point having a downwardly convex shape. For example, the local minimum point may refer to a point of a graph where the graph changes from increasing to decreasing, or the smallest value of the graph within a given range.

In another example, the characteristic point extractor 310 may extract a point in a predetermined region of the bio-signal 40 where the amplitude is the maximum as an additional characteristic point, as shown in FIG. 4C. In this case, the predetermined region of the bio-signal 40 refers to a systolic phase of the blood pressure from the beginning of the bio-signal 40 to the point of the dicrotic notch (DN). The dicrotic notch may refer to an acute drop followed by a rise in blood pressure pulse curves, which appears subsequent to a systolic peak. For example, a position where the bio-signal 40 is curved or bulged downward between time points $T_2$ and $T_3$ may correspond to the dicrotic notch. When the bio-signal 40 is acquired, the characteristic point extractor 310 may extract time points $T_1$, $T_2$, and $T_3$ and amplitudes $P_1$, $P_2$, and $P_3$ from each of the three component pulses 41, 42, and 43 constituting the bio-signal 40 as characteristic points, and extract a time point $T_{max}$ and an amplitude $P_{max}$ at a point where the systolic phase of the blood pressure as additional characteristic points. In this case, as described above, the characteristic point extractor 310 may derive a second derivative signal and extract characteristic points by searching for local minimum points of the second derivative signal.

In another example, the characteristic point extractor 310 may extract an area $S_{area}$ of the bio-signal waveform, for example, the whole area or a partial area as characteristic points. At this time, the partial area may mean the area of the bio-signal waveform corresponding to a time region from the beginning to a predetermined ratio (e.g., 70%) based on a time axis of the bio-signal waveform.

However, examples of the characteristic point extraction of the bio-signal are not limited to the above description, and the characteristic points may be extracted using other various methods.

When the characteristic points are extracted from the bio-signal as described above, the feature extractor 330 may combine the extracted characteristic points to extract features for bio-information estimation. However, if only the points associated with the component pulses are extracted as described, it may be difficult to extract stable characteristic points and feature when noise is contained in the bio-signal waveform or an unstable waveform occurs in a moving environment. Therefore, according to the present exemplary embodiment, the internally dividing point calculator 320 may calculate internally dividing points using the characteristic points extracted by the characteristic point extractor 310, thereby allowing the calculated internally dividing points to be used along with the extracted characteristic points in feature extraction.

Figure 5A:
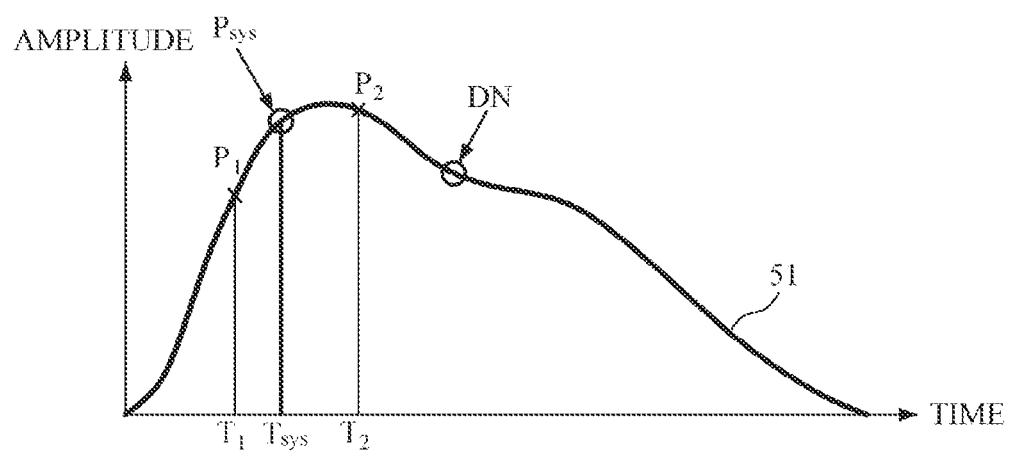
FIGS. 5A, 5B, 5C, 5D, and 5E are diagrams for describing an exemplary embodiment in which internal dividing points are calculated using the characteristic points of the bio-signal.
Figure 5B:
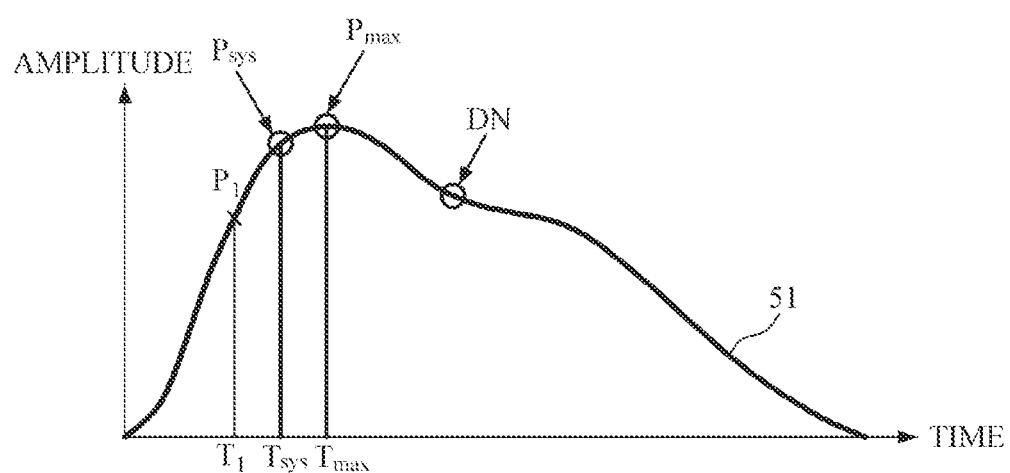

FIGS. 5A and 5B are diagrams illustrating examples in which the internally dividing point calculator 320 calculates an internally dividing point in a systolic region. The systolic region may refer to a region between the beginning of an acquired pulse wave signal 51 and the dicrotic notch (DN).

Referring to FIG. 5A, the internally dividing point calculator 320 may calculate an internally dividing point ($T_{sys}$, $P_{sys}$) between two characteristic points ($T_1$, $P_1$) and ($T_2$, $P_2$) using the two characteristic points ($T_1$, $P_1$) and ($T_2$, $P_2$) associated with a component pulse extracted from the systolic region by the characteristic point extractor 310. For example, the internally dividing point calculator 320 may apply weights a and b respectively to each time value $T_1$ and $T_2$ of the two characteristic points ($T_1$, $P_1$) and ($T_2$, $P_2$), and calculate the internally dividing point $T_{sys}$ using each of the time values $aT_1$, $bT_2$ to which the weights are applied. For example, the internally dividing point calculator 320 may obtain the internally dividing point $T_{sys}$ by summing the time values $aT_1$ and $bT_2$ to which the weights are applied and dividing the sum of the time values by the sum of the weights. Each of the weights a and b may be determined based on the amplitudes $P_1$ and $P_2$ of the respective characteristic points, and the internally dividing point $T_{sys}$ may be calculated as shown in Equation 1:

$$T_{sys}=(P_1\times T_1+P_2\times T_2)/(P_1+P_2) \quad (1)$$

However, the exemplary embodiment is not limited to the above examples, and the weight to be applied to each of the time points may be an arbitrary constant predefined through a preprocessing operation. As such, when the internally dividing point time $T_{sys}$ is determined, it is possible to extract the amplitude $P_{sys}$ at a point of the bio-signal corresponding to $T_{sys}$.

Referring to FIG. 5B, the internally dividing point calculator 320 may calculate an internally dividing point between two characteristic points $(T_1, P_1)$ and $(T_{max}, P_{max})$ using the two characteristic points $(T_1, P_1)$ and $(T_{max}, P_{max})$ extracted from a systolic region of the bio-signal 51. Similarly, the internally dividing point calculator 320 may apply weights respectively to each of the time values $T_1$ and $T_{max}$ of the two characteristic points $(T_1, P_1)$ and $(T_{max}, P_{max})$ and calculate an internally dividing point $T_{sys}$ using each of the time values to which the weights are applied. For example, the internally dividing point $T_{sys}$ may be calculated as shown in Equation 2:

$$T_{sys}=(P_1\times T_1+P_{max}\times T_{max})/(P_1+P_{max}) \quad (2)$$

The exemplary embodiment of FIG. 5B is useful when a waveform of the bio-signal 51 is not ideal and exhibits instability. For example, in the case of an abnormal waveform, a waveform component corresponding to the second characteristic point $(T_2, P_2)$ may not be accurately observed. In this case, instead of the second characteristic point $(T_2, P_2)$, a characteristic point $(T_{max}, P_{max})$ at which the amplitude is the maximum in the systolic region may be used to obtain an internally dividing point $(T_{sys}, P_{sys})$ robust to the abnormal waveform. In addition, in a case where a waveform of the bio-signal is unstable, a value of $P_1$ of the first characteristic point in an environment where characteristic points are continuously measured may be suddenly observed as a very small value. Even in this case, if an amplitude value $P_{max}$ at a point where the amplitude is the maximum in the systolic region is maintained constant, by giving a weight based on the amplitude values $P_1$ and $P_{max}$, a robust internally dividing point $(T_{sys}, P_{sys})$ may be obtained in spite of the instability of the characteristic point $(T_1, P_1)$.

Figure 5C:
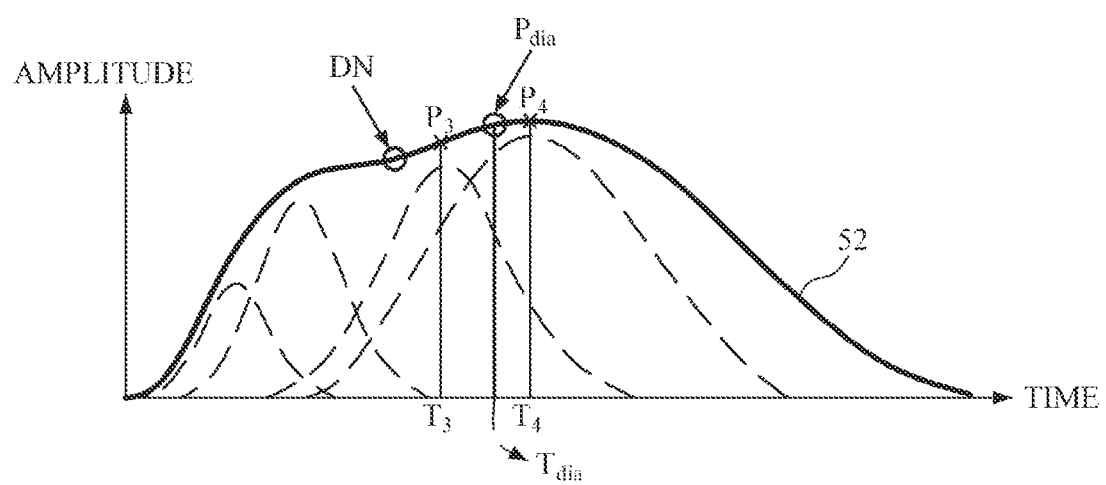
Figure 5D:
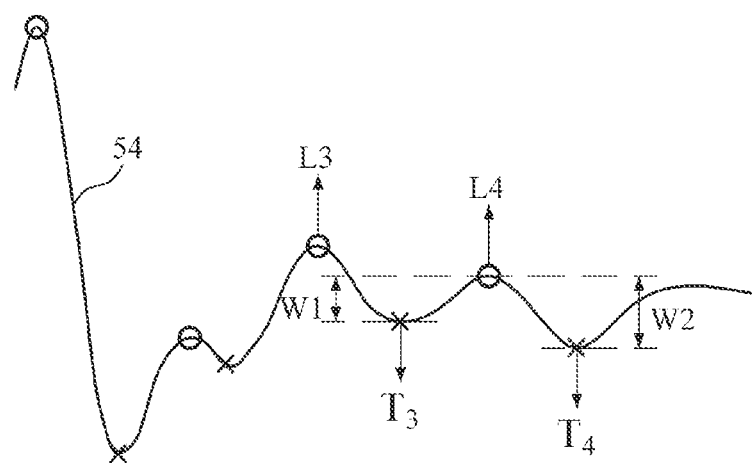
Figure 5E:
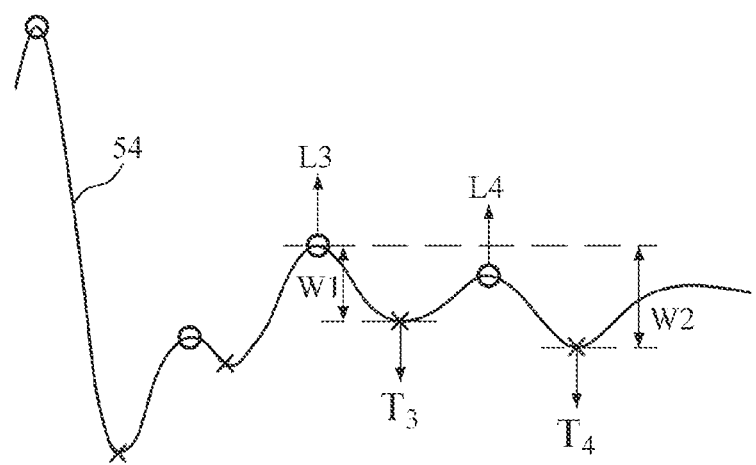

FIGS. 5C to 5E are diagrams for describing an exemplary embodiment in which an internally dividing point in the diastolic region is calculated. The diastolic region may refer to a region of a bio-signal after dicrotic notch (DN).

Referring to FIG. 5C, the characteristic point extractor 310 may extract a point $(T_3, P_3)$, which is a point associated with the third component pulse, as a representative characteristic point in the diastolic region of a pulse wave signal 52. This characteristic point increases in instability relative to a characteristic point extracted from the diastolic region due to various noises generated. According to the present exemplary embodiment, the internally dividing point calculator 320 may calculate an internally dividing point by utilizing a characteristic point of another component pulse in the systolic region.

For example, as shown in FIG. 5C, when it is assumed that generally the third component pulse associated with the characteristic point $(T_3, P_3)$ is a waveform component having the largest maximum amplitude in the diastolic region of a bio-signal, a characteristic point $(T_4, P_4)$ associated with a waveform component having an amplitude greater than an amplitude of the amplitude $P_3$, for example, a waveform component of the fourth component pulse in the diastolic region may be extracted in the case of a specific bio-signal waveform. In this case, physiologically, the characteristic point $(T_3, P_3)$ associated with the third component pulse may not be given great significance. At this point, the internally dividing point calculator 320 may calculate an internally dividing point (Tam, Pam) of the characteristic points $(T_3, P_3)$ and $(T_4, P_4)$ extracted from the diastolic region. The internally dividing point calculator 320 may apply weights respectively to each of the time points $T_3$ and $T_4$ based on each of the amplitudes $P_3$ and $P_4$, and calculate the internally dividing point (Tam, Pam) in the diastolic region based on the time values to which the weights are applied. For example, the internally dividing point $(T_{dia}, P_{dia})$ may be calculated as shown in Equation 3:

$$T_{dia}=(P_3\times T_3+P_4\times T_4)/(P_3+P_4) \quad (3)$$

Meanwhile, the internally dividing point calculator 320 may determine whether a preset condition of calculating the internally dividing point in the diastolic region is satisfied, and, when the condition is satisfied, may calculate the internally dividing point. In this case, the condition for calculating the internally dividing point in the diastolic region may be satisfied when the value of $P_3$ is smaller than the value of $P_4$. When it is determined that the value of $P_3$ is greater than the value of $P_4$, the characteristic point $(T_3, P_3)$ extracted from the third component pulse may be used as is. However, the condition for calculating the internally dividing point is not limited to the above description, and the condition may include a case where a difference between $P_3$ and $P_4$ is not greater than an arbitrary number, a case where a difference between $P_3$ and $P_4$ is greater than an arbitrary number, or the like.

In another example, the internally dividing point calculator 320 may calculate the internally dividing point based on an n-order derivative signal of the bio-signal in the diastolic region. The characteristic point extractor 310 may search for local minimum points of a second derivative signal by second order differentiating the bio-signal and extract characteristic points associated with component pulses, as described above. In this case, if the bio-signal has been acquired in a non-ideal environment and thus the waveform of the bio-signal is unstable, the second derivative signal may also fluctuate unstably. For example, the local minimum point of the second derivative signal corresponding to the representative characteristic point $(T_3, P_3)$ of the diastolic region does not appear at the physiologically correct position, and the local minimum point of the second derivative signal may unsteadily fluctuate back and forth around the corresponding position.

In this case, the internally dividing point calculator 320 may calculate an internally dividing point of characteristic points extracted from two local minimum points of the second derivative signal in order to alleviate the instability of the second derivative signal. The internally dividing point calculator 320 may apply a weight to each of the time values of the characteristic points based on a difference between the amplitude of each of the local minimum points of the second derivative signal and the amplitude at a predetermined point of the second derivative signal, and calculate the internally dividing point using each of the time values to which the weights are applied, as described above.

For example, referring to FIG. 5D, a difference $W_1$ between the amplitude of $T_3$, which is a local minimum point of a diastolic region of a second derivative signal 54, and the amplitude of a local maximum point $L_4$, which appears immediately before $T_4$, may be determined as a weight to be applied to the time value $T_3$ of a characteristic point in the diastolic region. In addition, a difference $W_2$ between the amplitude of $T_4$, which is a local minimum point, and the amplitude of $L_4$, which is a local maximum point, may be determined as a weight of the time value $T_4$ of a characteristic point of the diastolic region. The time value $T_3$ may be referred to as a third local minimum point given that the time value $T_3$ is a local minimum point that thirdly appears in the diastolic region of the second derivative signal 54. The time value $T_4$ may be referred to as a fourth local minimum point given that the time value $T_4$ is a local minimum point that fourthly appears in the diastolic region of the second derivative signal 54. According to the exemplary embodiment of FIG. 5D, the internally dividing point $(T_{dia}, P_{dia})$ may be calculated as shown in Equation 4:

$$T_{dia}=(W_1 \times T_3 + W_2 \times T_4)/(W_1+W_2) \qquad (4)$$

FIG. 5E shows an example in which differences between the amplitude of $T_3$ and the amplitude of $L_3$ and between the amplitude of $T_4$ and the amplitude of $L_3$ are determined as weights $w_1$ and $w_2$ to be applied respectively to time values $T_3$ and $T_4$ of characteristic points of the diastolic region.

Meanwhile, the internally dividing point calculator 320 may determine whether a condition for calculating an internally dividing point is satisfied based on at least one of the weights $w_1$ and $w_2$, which are obtained based on the second derivative signal, and when the condition is satisfied, may calculate the internally dividing point. For example, only when the weight $w_1$ to be applied to the first characteristic point $(T_3, P_3)$ in the diastolic region is smaller than a predetermined threshold, the internally dividing point may be calculated. If the weight $w_1$ is greater than or equal to the predetermined threshold, the first characteristic point $(T_3, P_3)$ may be used as is without the weight $w_1$ being applied. However, the exemplary embodiment is not limited thereto, and the condition for calculating the internally dividing point may include various conditions, such as a case where the $w_2$ to be applied to the second characteristic point $(T_4, P_4)$ in the diastolic region is greater than a predetermined threshold.

Once the characteristic points and the internally dividing points are obtained, the feature extractor 330 may determine information to be used in feature extraction among the obtained characteristic points and internally dividing points, and extract features necessary for bio-information extraction by combining the determined information.

For example, it is assumed that $(T_1, P_1)$, $(T_3, P_3)$, $(T_4, P_4)$, $(T_{max}, P_{max})$, and $S_{area}$ are extracted by the characteristic point extractor 310. In addition, it is assumed that an internally dividing point $(T_{sys}, P_{sys})$ between the characteristic points $(T_1, P_1)$ and $(T_{max}, P_{max})$ and an internally dividing point $(T_{dia}, P_{dia})$ between the characteristic points $(T_3, P_3)$ and $(T_4, P_4)$ are calculated. In this case, through an analysis of bio-signal waveform, second derivative signal waveform, and component pulses, the feature extractor 330 may determine the calculated internally dividing points $(T_{sys}, P_{sys})$ and $(T_{dia}, P_{dia})$, the characteristic point $(T_{max}, P_{max})$, and $S_{area}$ as information to be used in feature extraction. In addition, the feature extractor 330 may acquire two features $f_1$ and $f_2$ as shown in Equation 5 below by combining the determined information.

$$f_1 = P_{max}/S_{area}$$

$$f_2 = 1/(T_{dia} - T_{sys}) \qquad (5)$$

However, the features are merely examples, and are not limited thereto. For example, the first feature $f_1$ is a feature related to the cardiac output, and it may further include, such as, $P_{max}/P_{area}$, $P_{max}/P_3$, $P_{sys}/P_3$, $P_1/P_3$, $P_2/P_3$, $1/T_{period}$, or the like. The second feature $f_2$ is a feature related to the total peripheral vascular resistance, and it may further include $1/(T_3-T_{sys})$, $1/(T_3-T_{max})$, $1/(T_3-T_1)$, $1/(T_3-T_2)$, $P_3/P_1$, $P_2/P_1$, or the like. Here, $P_{area}$ denotes the sum of amplitudes of the bio-signal for a predefined time interval (e.g. between time 0 and $\tau_{dur} \ast T_{period}$). $T_{period}$ denotes a period of the bio-signal. $\tau_{dur}$ denotes a predefined setting factor $(0 \leq \tau_{dur} \leq 1)$ (e.g., 0.7).

When the feature extractor 320 extracts the features, the bio-information estimator 340 may estimate bio-information using the extracted features. For example, blood pressure may be estimated by applying the features extracted as shown in the above Equation 5 to a blood pressure estimation equation as shown in Equation 6 below.

$$BP = A(f_1 + wf_2) + B \qquad (6)$$

Here, BP denotes an estimated blood pressure, and A, w, and B denote arbitrary coefficients.

Figure 6A:
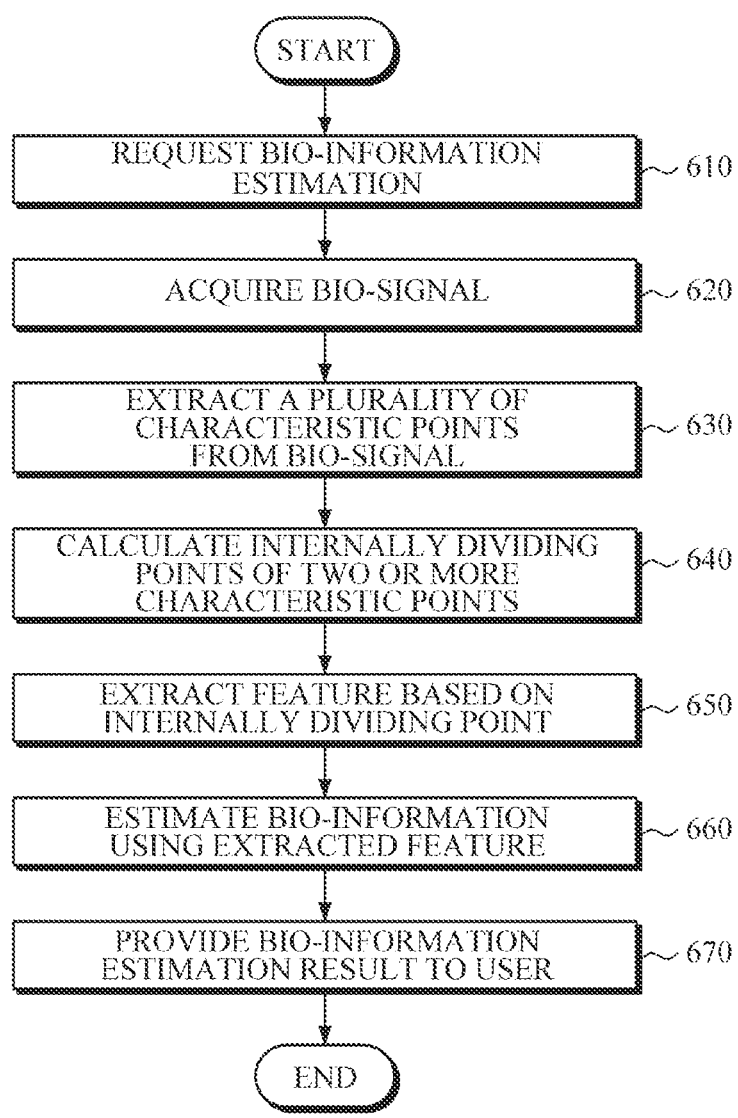
FIGS. 6A, 6B, and 6C are flowcharts illustrating a method of estimating bio-information according to one exemplary embodiment.

FIG. 6A is a flowchart illustrating a method of estimating bio-information according to one exemplary embodiment.

FIG. 6A shows an exemplary embodiment of a method of estimating bio-information which is performed by the apparatus 100 for estimating bio-information according to the exemplary embodiment of FIG. 1, which has been described in detail with reference to FIGS. 1 to 5E, and thus the method will be described in brief to avoid unnecessary repetition.

First, the apparatus 100 for estimating bio-information receives a request for bio-information estimation, in operation 610. The apparatus 100 may provide an interface to perform various interactions with a user. The user may request the bio-information estimation through the interface provided by the apparatus 100.

Alternatively, the apparatus 100 may receive a request for bio-information estimation from an external device. In this case, the request for bio-information estimation received from the external device may include a request for providing a bio-information estimation result. When the external device is equipped with a bio-information estimation algorithm, the request for bio-information estimation may include a request for providing characteristic point or feature information. The external device may include a smartphone or a tablet PC that the user carries, and the user may control the apparatus 100 through a portable device having superior interface performance and computing performance to those of the apparatus 100 for bio-information estimation.

Then, the apparatus 100 acquires a bio-signal for bio-information estimation, in operation 620. For example, the apparatus 100 may control a bio-signal measurement sensor (e.g., a PPG sensor) to measure a pulse wave signal, and acquire a pulse wave signal from an object. In another example, when the apparatus 100 does not include the bio-signal measurement sensor, the apparatus 100 may receive a bio-signal from an external bio-signal measurement device.

Then, a plurality of characteristic points may be extracted from the acquired bio-signal, in operation 630. As described above, the apparatus 100 may extract points associated with component pulses constituting the acquired bio-signal as the characteristic points. For example, the apparatus 100 may acquire a second derivative signal of a pulse wave signal acquired for estimating blood pressure, and extract information about time and amplitude of a local minimum point of the second derivative signal as a characteristic point associated with a component pulse. In addition, the apparatus 100 may extract time and amplitude information at a point where the amplitude is the maximum in a systolic phase of blood pressure as an additional characteristic point in order to compensate the case where the pulse wave signal is unstable due to noise, motion, or the like. Also, the apparatus 100 may extract the whole area or a partial area of the pulse wave signal as an additional characteristic point.

Thereafter, internally dividing points of two or more characteristic points are calculated, in operation 640. For example, the apparatus 100 may calculate an internally dividing point for each of the systolic region and the diastolic region of the pulse wave signal. Two time values extracted from the pulse wave signal may be given weights and an internally dividing point may be calculated using the time values to which the weights are applied. In this case, the weights may be determined based on the amplitude values of two characteristic points. For example, the internally dividing point may be calculated by dividing the sum of the time values to which the weights are applied by the sum of the weights. Meanwhile, when the plurality of characteristic points are extracted, the apparatus 100 may check various preset conditions for calculating an internally dividing point, and may use the extracted characteristic points intact when the conditions are not satisfied.

Then, the apparatus 100 extracts features necessary for bio-information estimation using the extracted characteristic points and internally dividing points, in operation 650. In this case, the features necessary for bio-information estimation may be extracted by combining two or more characteristic points and internally dividing points as shown in Equation 5.

Hereinafter, operations 630 to 650 are described with references to FIGS. 6B and 6C in greater detail.

Figure 6B:
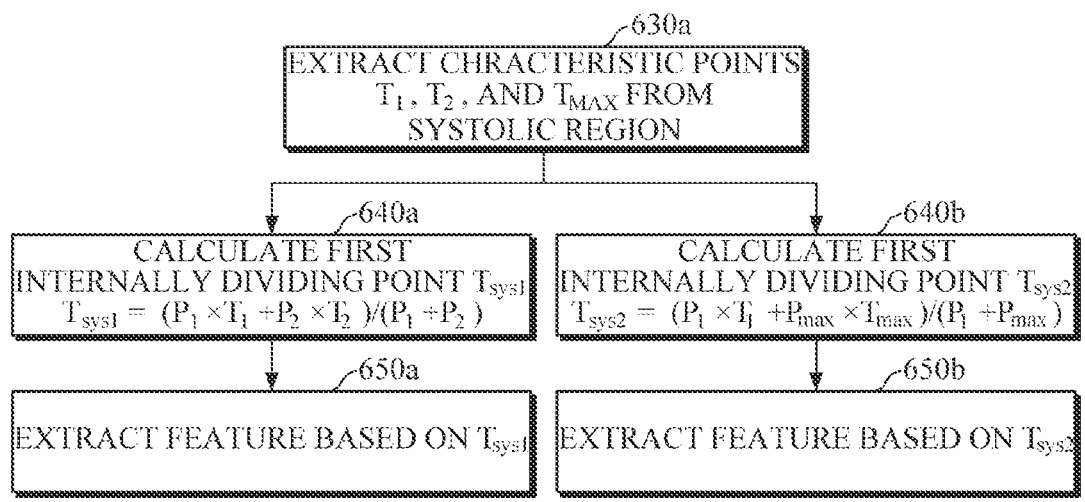

As shown in FIG. 6B, the apparatus 100 may extract characteristic points $(T_1, P_1)$, $(T_2, P_2)$, and $(T_{max}, P_{max})$ from the systolic region of the pulse wave signal, in operation 630*a*. In turn, the apparatus 10 may calculate a first internally dividing point $T_{sys1}$ according to equation 1 in operation 640*a*, and may calculate a second internally dividing point $T_{sys2}$ according to equation 2 in operation 640*b*. The apparatus 100 may perform either operation 640*a* or operation 640*b*, or both of the operations 640*a* and 640*b*. Then, the apparatus 100 may extract features based on the first internally dividing point $T_{sys1}$ and the second internally dividing point $T_{sys2}$ in operations 650*a* and 650*b*, respectively.

Figure 6C:
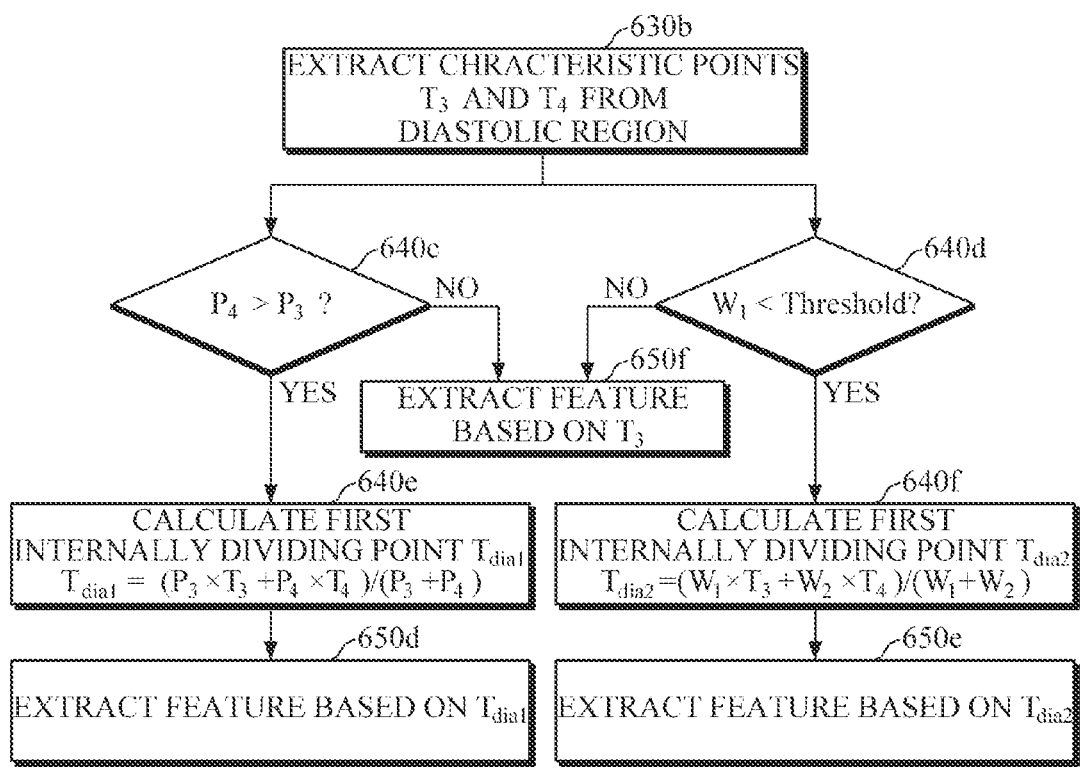

As shown in FIG. 6C, the apparatus 100 may extract characteristic points $(T_3, P_3)$ and $(T_4, P_4)$ from the diastolic region of the pulse wave signal, in operation 630*b*. If the apparatus 100 determines that the amplitude $P_4$ is greater than the amplitude $P_3$ in operation 640*c*, the apparatus 100 may calculate a first internally dividing point $T_{dia1}$ for the diastolic region according to Equation 3, in operation 640*e*, and extract a feature based on $T_{dia1}$ in operation 650*d*. On the other hand, if the apparatus 100 determines that the amplitude $P_4$ is less than or equal to the amplitude $P_3$ in operation 640*c*, the apparatus 100 may extract a feature based on the characteristic point $(T_3, P_3)$.

Alternative to operations 640*c*, 640*e*, and 650*b*, the apparatus 100 may determine whether a difference $W_1$ between the amplitude at a local minimum point $T_3$ of the second derivative signal 54 and the amplitude at a local maximum point $L_4$ immediately before $T_4$ is less than a predetermined threshold, in operation 640*d*. In another example, the different $W_1$ may correspond to the difference between the amplitude at $T_3$ and the amplitude at a local maximum point $L_3$ immediately before $T_4$. In operation 640*f*, the apparatus 100 may calculate a second internally dividing point $T_{dia2}$ for the diastolic region according to Equation 4, and then in operation 650*e*, the apparatus 100 may extract a feature based on the second internally dividing point $T_{dia2}$. However, if the apparatus 100 determines that the difference $W_1$ is equal to or greater than the predetermined threshold in operation 640*d*, the apparatus 100 may extract a feature based on the characteristic point $(T_3, P_3)$ instead of the second internally dividing point $T_{dia2}$ in operation 650*f*.

Operations 630*a*, 640*a*, 640*b*, 650*a*, and 650*b* shown in FIG. 6B, and operations 630*b*, 640*c*-640*f*, and 650*d*-650*f* shown in FIG. 6*c* may be performed in parallel or in sequence.

Then, the apparatus 100 estimates bio-information using the extracted features, in operation 660. In this case, a bio-information estimation model may be constructed in advance. The bio-information estimation model may be a mathematical equation as shown in Equation 6. When the features are extracted, the apparatus 100 may estimate the bio-information by applying the extracted feature information to the bio-information estimation model.

Then, the apparatus 100 provides a bio-information estimation result to the user, in operation 670. At this time, the apparatus 100 may provide the estimated bio-information to the user using various visual/non-visual methods. In addition, the apparatus 100 may determine the user's health status based on the estimated bio-information, and provide warning or an advice on actions to be taken to the user according to the determination result.

FIGS. 7A to 7D are diagrams for describing a wearable device according to one exemplary embodiment. Various exemplary embodiments of the above-described apparatus for estimating bio-information may be mounted in a smartwatch or smart band-type wearable device worn on a wrist. However, this is merely an example for convenience of description, and the exemplary embodiments should not be construed as being limited to being applied to a smart watch or smart band-type wearable device.

Referring to FIGS. 7A to 7D, a wearable device 700 includes a device main body 710 and a strap 720.

The strap 720 may be configured to be flexible and bent in such a manner that is wrapped around the wrist of the user or separated from the wrist. Alternatively, the strap 720 may be configured in a non-separable band form. In this case, the strap 720 may be filled with air or an air bag so as to have elasticity according to a change in pressure applied to the wrist, and may transmit a pressure change of the wrist to the main body 710.

A battery may be equipped in the main body 710 or the strap 720 to supply power to the wearable device.

In addition, the wearable device 700 may include, inside the main body 710, a measurer 711 configured to measure a bio-signal by emitting light to an object OBJ and detecting scattered light returning from the object OBJ, and a processor 712 configured to detect bio-information of the user using the bio-signal measured by the measurer 711.

The measurer 711 may be mounted on a lower portion of the main body 710, that is, a portion that comes in contact with the object OBJ, for example, the user's wrist, and may include a light source 711A configured to emit light to the object OBJ and a detector 711B configured to detect light emitted from the object OBJ according to a control signal of the processor 712.

In addition, the measurer 711 may further include a contact pressure sensor configured to measure a contact pressure of the object OBJ. The contact pressure sensor may measure the contact pressure of the object OBJ transferred to the main body 710 through the strap 720 that secures the main body to the object OBJ in a manner that is wrapped around the wrist.

The processor 712 may generate the control signal to control the measurer 711. In addition, the processor 712 may receive bio-signal data measured by the measurer 711 and estimate bio-information using the bio-signal data.

For example, the processor 712 may extract a plurality of characteristic points from the bio-signal as described above. In this case, the plurality of characteristic points may be extracted from points associated with component pulses of the bio-signal. In addition, a point where the amplitude is the maximum within a predetermined region of the bio-signal or an area of the bio-signal may be extracted as characteristic points.

When the plurality of characteristic points are extracted from the bio-signal, the processor 712 may calculate internally dividing points of two or more characteristic points and extract features using the calculated internally dividing points and the characteristic points. The processor 712 may determine characteristic points to be used to calculate the internally dividing points according to a preset criterion for calculating the internally dividing points, apply weights to time values of two or more determined characteristic points, and calculate the internally dividing points based on the time values to which the weights are applied. In this case, the weights respectively applied to each of the time values may be determined based on amplitude values of each of the two or more determined characteristic points.

When the contact pressure sensor is equipped in the measurer 711 and measures a contact pressure signal of the object, the processor 712 may guide the user to change the contact pressure applied to the wrist based on the measured contact pressure signal.

The processor 712 may manage estimated bio-information, for example, blood pressure history information, bio-information used to measure various blood pressures, and component pulses decomposed from the bio-information in a storage device. Also, the processor 712 may generate additional information, such as alarm or warning information related to estimated bio-information, a change in health status, and the like, which is necessary for user's healthcare and manage the generated information in the storage device.

In addition, the wearable device 700 may further include an operator 715 and a display 714, which are mounted in the main body 710.

The operator 715 may receive a control instruction of the user, transmit the control instruction to the processor 712, and include a power button to enable the user to input an instruction for power on/off of the wearable device 700.

The display 714 may provide a variety of information related to the detected bio-information under the control of the processor 712. For example, the display 714 may display additional information, such as measured blood pressure, alarm, or warning information, to the user in various visual/non-visual ways.

Figure 7A:
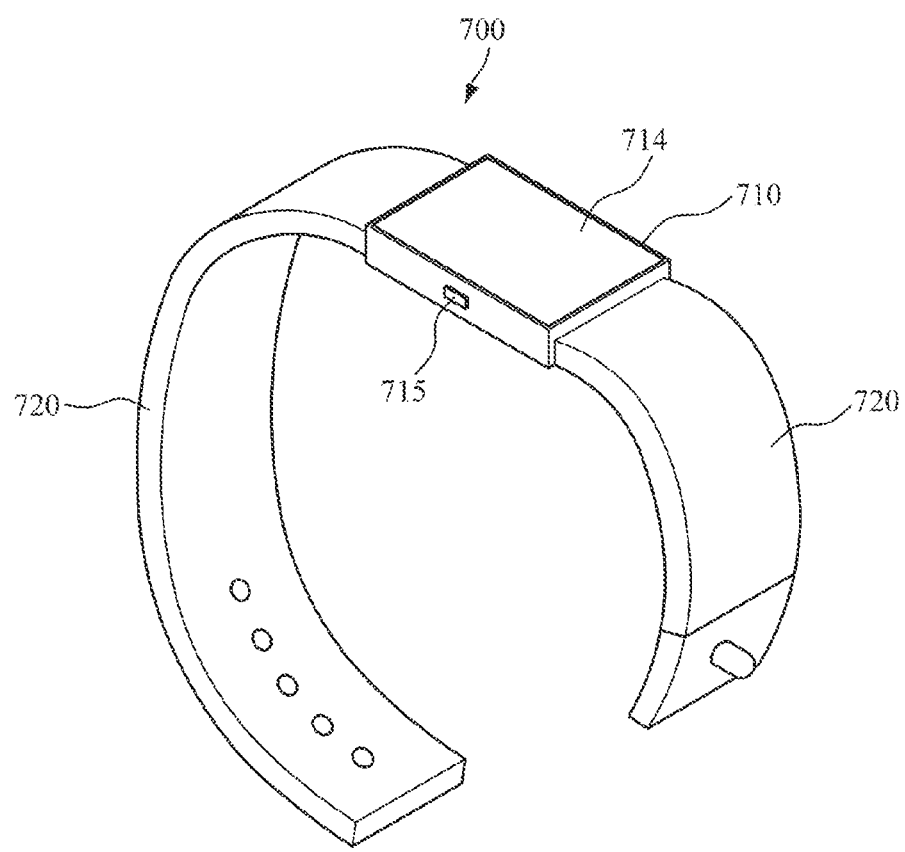
FIGS. 7A, 7B, 7C, and 7D are diagrams for describing a wearable device according to one exemplary embodiment.
Figure 7B:
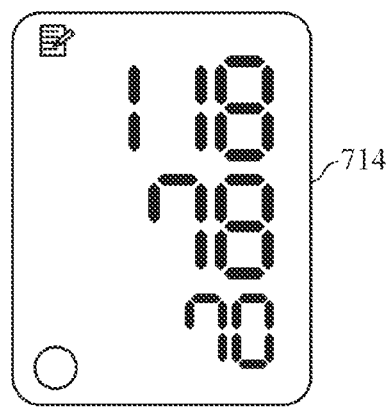
Figure 7C:
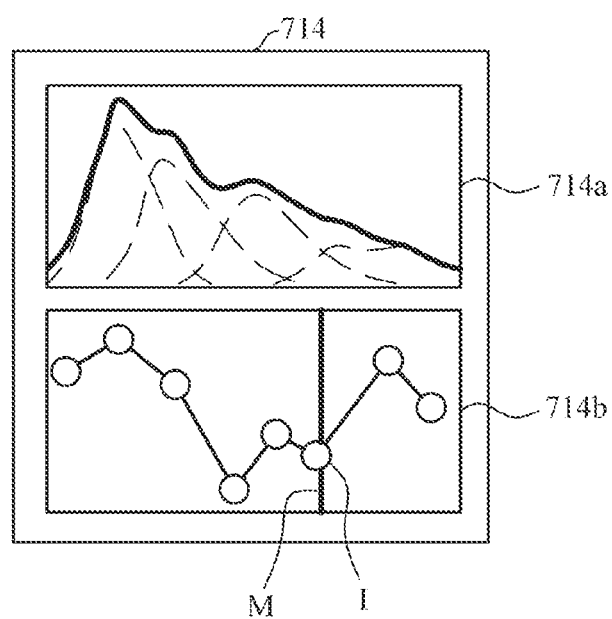
Figure 7D:
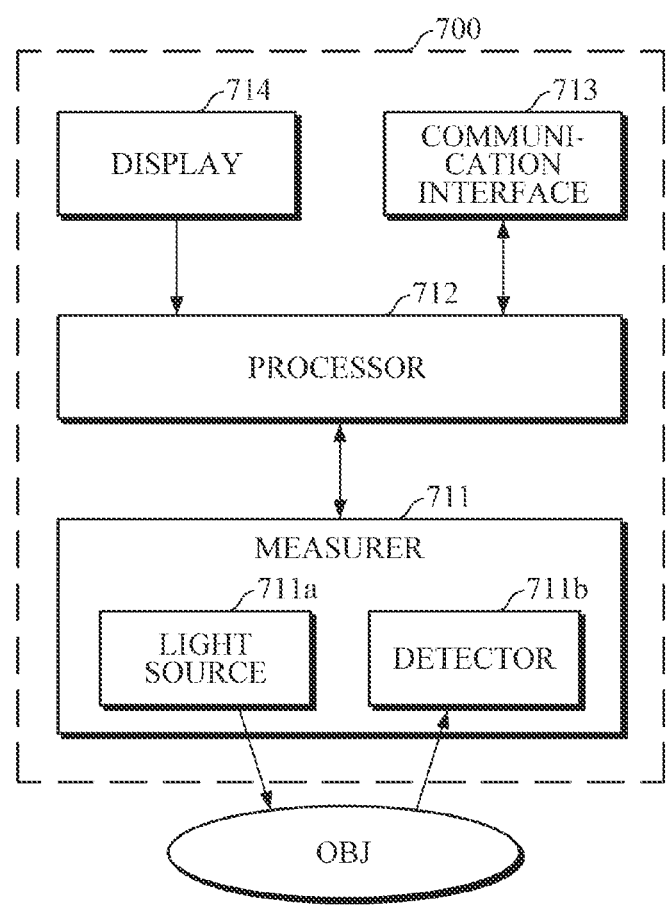

For example, referring to FIGS. 7B and 7C, when blood pressure is estimated according to a user's request, the display 714 may display estimated blood pressure information as shown in FIG. 7B. Also, when the user requests detailed information by controlling the operator 715 or touching the display 714, the display 714 may display the detailed information as shown in FIG. 7C. For example, as shown in FIG. 7C, the display 714 may include a first area 714b and a second area 714a. The estimated blood pressure information may be displayed in the first area 714b, as shown in FIG. 7B. Alternatively, as shown in FIG. 7C, the change in blood pressure may be displayed in the form of a graph.

The display 714 may display a mark M that indicates currently selected blood pressure information I in the first area 714b. In FIG. 7C, the mark M is shown as a vertical line, but is not limited thereto, and the mark M may be displayed in various forms, such as a polygon, such as a circle, a rectangle, and the like, and an arrow indicating a position of the selected blood pressure information. When the change in blood pressure is displayed in the first area 714b, the user may touch and select desired blood pressure information or select the desired blood pressure information by moving the graph to the left and right to align the desired blood pressure information to the mark M. When the user selects the blood pressure information in the first area 714b, blood pressure information, extracted feature information, and the like may be displayed near the selected blood pressure information.

In addition, when the user selects any blood pressure information in the first area 714b, the display 714 may display a bio-signal used to estimate the selected blood pressure information I in response to the user's selection, and component pulses constituting the bio-signal in the second area 714a. In addition, extracted characteristic points may be displayed on the bio-signal shown in the second area 714a. By doing so, the user may easily grasp the change of the blood pressure and intuitively understand the bio-signal and a variety of information extracted from the bio-signal according to the change of the blood pressure.

In addition, the main body 710 may further include a communication interface 713 in an internal space so as to communicate with an external device, such as a portable terminal of the user.

The communication interface 713 may communicate with the external device of a user which has a relatively better computing performance and transmit and receive necessary information under the control of the processor 712. For example, the communication interface 713 may receive a request for estimating bio-information from the user's portable terminal. In addition, the communication interface 713 may transmit extracted characteristic points or feature information to the external device to request estimation of bio-information. Further, the communication interface 713 may transmit a bio-information estimation result to the external device so as to be displayed to the user or to be utilized for various purposes, such as bio-information history management and disease research.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A blood pressure monitoring device, comprising:
a light emitter configured to emit a light to a subject;
a light detector configured to detect the light that is scattered, deflected, or reflected from the subject to obtain a pulse wave signal from the detected light;
a processor configured to;
  extract a first time point $T_1$ and a second time point $T_2$ from the pulse wave signal, as a plurality of characteristic points, when the pulse wave signal comprises a first component pulse wave that has a maximum amplitude at the first time point $T_1$, and a second component pulse wave that has a maximum amplitude at the second time point $T_2$;
  determine, as amplitude values corresponding to the plurality of characteristic points, a first amplitude $P_1$ and a second amplitude $P_2$ of the pulse wave signal corresponding to the first time point $T_1$ and the second time point $T_2$, respectively;
  determine the internally dividing points of the plurality of characteristic points by dividing a sum of a product of the first amplitude $P_1$ and the first time point $T_1$, and a product of the second amplitude $P_2$ and the second time point $T_2$, by a sum of the first amplitude $P_1$ and the second amplitude $P_2$; and
  determine a blood pressure of the subject based on the internally dividing points of the pulse wave signal; and
a display configured to display a graph of the blood pressure of the subject which has been measured over time, and display a mark configured to move along the graph of the blood pressure according to a user input to allow the user to select a specific blood pressure data point from the graph.

2. The blood pressure monitoring device of claim 1, wherein the processor is further configured to:
  extract a third time point $T_3$ and a fourth time point $T_4$ from the pulse wave signal, as the plurality of characteristic points, when the pulse wave signal comprises a third component pulse wave that has a maximum amplitude at the third time point $T_3$, and a fourth component pulse wave that has a maximum amplitude at the fourth time point $T_4$;
  determine, as the amplitude values corresponding to the plurality of characteristic points, a third amplitude $P_3$ and a fourth amplitude $P_4$ of the pulse wave signal corresponding to T3 and T4, respectively; and
  determine the internally dividing points further based on the third time point $T_3$, the fourth time point $T_4$, the third amplitude $P_3$, and the fourth amplitude $P_4$, in response to the fourth amplitude $P_4$ being greater than the third amplitude $P_3$.

3. The blood pressure monitoring device of claim 1, wherein the processor is further configured to:
  extract, as the plurality of characteristic points, a third local minimum point $T_{local3}$ and a fourth local minimum point $T_{local4}$ from a second derivative signal of the pulse wave signal;
  extract, from the second derivative signal, a third local maximum point $L_3$ that appears prior to the third local minimum point $T_{local3}$, and a fourth local maximum point $L_4$ that appears between the third local minimum point $T_{local3}$ and the fourth local minimum point $T_{local4}$, as the plurality of characteristic points; and
  determine a first difference $W_1$ between an amplitude at the third local minimum point $T_{local3}$ and an amplitude at the fourth local maximum point $L_4$;
  determine a second difference $W_2$ between the amplitude at the fourth local maximum point $L_4$ and an amplitude at the fourth local minimum point $T_{local4}$; and
  determine the internally dividing points further based on the third local minimum point $T_{local3}$, the fourth local minimum point $T_{local4}$, the first difference $W_1$, and the second difference $W_2$.

4. The blood pressure monitoring device of claim 1, wherein the processor is further configured to:
  extract, as the plurality of characteristic points, a third local minimum point $T_{local3}$ and a fourth local minimum point $T_{local4}$ from a second derivative signal of the pulse wave signal;
  extract, from the second derivative signal, a third local maximum point $L_3$ that appears prior to the third local minimum point $T_{local3}$, and a fourth local maximum point $L_4$ that appears between the third local minimum point $T_{local3}$ and the fourth local minimum point $T_{local4}$, as the plurality of characteristic points; and
  determine a first difference $W_1$ between an amplitude at the third local maximum point $L_3$ and an amplitude at the third local minimum point $T_{local3}$;
  determine a second difference $W_2$ between the amplitude at the third local maximum point $L_3$ and the amplitude at the fourth local minimum point $T_{local4}$; and
  in response to the first difference $W_1$ being less than a predetermined threshold value, determine the internally dividing points further based on the third local minimum point $T_{local3}$, the fourth local minimum point $T_{local4}$, the first difference $W_1$, and the second difference $W_2$.

5. The blood pressure monitoring device of claim 1, wherein the processor is further configured to determine whether the blood pressure is within a normal range, and wherein the blood pressure monitoring device further comprises:
  a vibrator configured to provide vibration which changes according to abnormality of the blood pressure.

6. A blood pressure monitoring device, comprising:
a light emitter configured to emit a light to a subject;
a light detector configured to detect the light that is scattered, deflected, or reflected from the subject to obtain a pulse wave signal from the detected light, wherein the pulse wave signal comprises at least a first component pulse wave, a second component pulse wave, a third component pulse wave, and a fourth component pulse wave;
a processor configured to:
  extract a first characteristic point set of $T_1$ and $P_1$, a second characteristic point set of $T_{max}$ and $P_{max}$, a third characteristic point set of $T_3$ and $P_3$, and a fourth characteristic point set of $T_4$ and $P_4$ from the pulse wave signal, wherein $P_1$ denotes a maximum amplitude of the first component pulse wave, $T_1$ denotes a time corresponding to $P_1$ in the first component pulse wave, $P_{max}$ denotes a maximum amplitude of the pulse wave signal, $T_{max}$ denotes a time corresponding to $P_{max}$ in the pulse wave signal, $P_3$ denotes a maximum amplitude of the third component pulse wave, $T_3$ denotes a time corresponding to $P_3$ in the third component pulse wave, $P_4$ denotes a maximum amplitude of the fourth component pulse wave, $T_4$ denotes a time corresponding to $P_4$ in the fourth component pulse wave, and $S_{area}$ denotes an area under the pulse wave signal;

acquire a first internally dividing point set of $T_{sys}$ and $P_{sys}$ between the first characteristic point set of $T_1$ and $P_1$ and the second characteristic point set of $T_{max}$ and $P_{max}$, and a second internally dividing point set of $T_{dia}$ and $P_{dia}$ between the third characteristic point set of $T_3$ and $P_3$, and the fourth characteristic point set of $T_4$ and $P_4$;

acquire a first feature based on a ratio between $P_{max}$ and $S_{area}$ and a second feature based on a difference between $T_{dia}$ and $T_{sys}$;

estimate a blood pressure of the subject based on a weight sum of the first feature and the second feature; and a display configured to display a graph of the blood pressure of the subject which has been measured over time, and display a mark configured to move along the graph of the blood pressure according to a user input to allow the user to select a specific blood pressure data point from the graph.

\* \* \* \* \*